United States Patent [19]

Okon et al.

[11] Patent Number: 5,196,618
[45] Date of Patent: Mar. 23, 1993

[54] METHOD FOR THE PREPARATION OF METHYL CHLORIDE FROM CARBON TETRACHLORIDE AND METHYL ALCOHOL

[75] Inventors: Toshihiro Okon; Takaaki Shimizu, both of Niigata, Japan

[73] Assignee: Shin-Etsu Chemical Co., Ltd., Tokyo, Japan

[21] Appl. No.: 843,848

[22] Filed: Feb. 28, 1992

[30] Foreign Application Priority Data

Mar. 1, 1991 [JP] Japan .................................. 3-077443
Mar. 26, 1991 [JP] Japan .................................. 3-086085

[51] Int. Cl.$^5$ .............................................. C07C 17/16
[52] U.S. Cl. ..................................... 570/258; 423/437
[58] Field of Search .......................... 570/258; 423/437

[56] References Cited

U.S. PATENT DOCUMENTS 4,423,024 12/1983 Wolford ............................... 423/437
4,935,565 6/1990 Harley et al. .

Primary Examiner—Howard T. Mars
Attorney, Agent, or Firm—Wenderoth, Lind & Ponack

[57] ABSTRACT

An improvement is proposed in the method for the preparation of methyl chloride from carbon tetrachloride and methyl alcohol by the reaction including the partial reactions of, first, the hydrolysis reaction of carbon tetrachloride with water to form hydrogen chloride and carbon dioxide and, second, the reaction of methyl alcohol with hydrogen chloride, each in the presence of a solid catalyst of zinc chloride supported on active carbon. The uncontrollable temperature increase when these reactions are performed on a single catalyst bed can be avoided by conducting the first partial reaction in a first reaction zone with a feed of carbon tetrachloride and water alone and the second partial reaction is conducted in a separate second reaction zone into which the gaseous mixture from the first zone and methyl alcohol are introduced. When carbon dioxide in the gaseous mixture from the first zone is removed therefrom prior to introduction of the mixture into the second reaction zone, the problems accompanying the separation of carbon dioxide from a gaseous mixture containing methyl chloride can be solved.

13 Claims, 1 Drawing Sheet

FIGURE
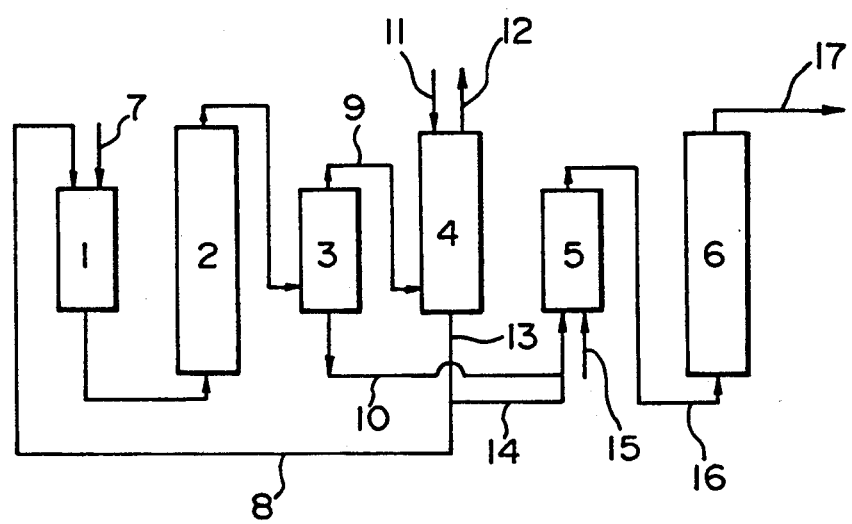

METHOD FOR THE PREPARATION OF METHYL CHLORIDE FROM CARBON TETRACHLORIDE AND METHYL ALCOHOL

BACKGROUND OF THE INVENTION

The present invention relates to a method for the preparation of methyl chloride from carbon tetrachloride and methyl alcohol as the starting materials. More particularly, the invention relates to an efficient method for the preparation of methyl chloride from carbon tetrachloride and methyl alcohol by the gas-phase reaction in the presence of a solid catalyst.

Methyl chloride, which is a useful chlorinated hydrocarbon compound consumed in large quantities, for example, in the synthesis of methyl chlorosilanes as the starting materials of silicone products, is produced, as a typical industrial process, by the chlorination reaction of methane which yields not only methyl chloride but also other higher chlorinated methanes including methylene chloride, chloroform and carbon tetrachloride by the successive unit reactions expressed by the reaction equations:

$$CH_4 + Cl_2 \rightarrow CH_3Cl + HCl;$$

$$CH_3Cl + Cl_2 \rightarrow CH_2Cl_2 + HCl;$$

$$CH_2Cl_2 + Cl_2 \rightarrow CHCl_3 + HCl; \text{ and}$$

$$CHCl_3 + Cl_2 \rightarrow CCl_4 + HCl.$$

These four reactions concurrently proceed in the reaction mixture so that the reaction product obtained by the process is always a mixture of these four kinds of chlorinated methane compounds, from which each of the compounds is to be isolated, for example, by distillation. A problem in this process is that, while the first three chlorinated compounds, i.e. methyl chloride, methylene chloride and chloroform, are useful and consumed in relatively large quantities as compared with carbon tetrachloride, the proportion of these four kinds of chlorinated compounds in the reaction mixture cannot be freely controlled so that overproduction of carbon tetrachloride is always unavoidable in the above described process of chlorination in order to satisfy the demand for the other three chlorinated methanes by continuedly practicing the process.

Therefore, it is an important technological issue to develop a method for converting carbon tetrachloride into some other more useful chemicals since otherwise carbon tetrachloride employed as such would ultimately be released to the atmosphere in the vapor form while, as is well known as a serious environmental problem, carbon tetrachloride is strongly suspected to be responsible for the destruction of the ozone layer in the stratosphere leading to an international agreement to entirely ban carbon tetrachloride by the end of this century reached in the London conference held in June, 1990.

Several proposals and attempts have been made heretofore for the conversion of carbon tetrachloride into other more useful and harmless chemical compounds, of which some are still in the laboratory stage and the others are already industrialized in a certain scale. Firstly, for example, carbon tetrachloride can be reduced with hydrogen in the presence of a catalyst such as Raney nickel into lower chlorinated methanes such as methyl chloride and methylene chloride. This method, however, is disadvantageous as an industrial process due to the low reaction velocity and limited life of the catalyst so that this method cannot be rendered to practice unless these problems could be solved in addition to the problem that by-products such as 1,2-dichloroethane and the like are produced in a large quantity.

Secondly, carbon tetrachloride can be burnt together with a fuel gas such as methane, liquefied petroleum gas and the like and converted into carbon dioxide and hydrogen chloride which can be recovered and utilized. This method is industrially disadvantageous due to the high reaction temperature of 1000° C. or even higher, at which the process of combustion can be proceed, and the corrosiveness of hydrogen chloride requiring a special structure of the furnace and an expensive high-grade corrosion-resistant refractory material for the furnace.

Thirdly, U.S. Pat. No. 4,423,024 proposes a method in which carbon tetrachloride is hydrolyzed in the vapor phase in the presence of a zeolite or molecular sieve catalyst. This method, which is conducted at a temperature of 240° to 330° C., also has a problem in the material of the reactor in addition to the relatively short life of the catalyst due to the deposition of tarry matters thereon as produced by the themal decomposition of carbon tetrachloride.

Fourthly, the inventors have previously proposed a method for the direct conversion of carbon tetrachloride into methyl chloride by a single step reaction of carbon tetrachloride with methyl alcohol in the presence of a solid catalyst such as zinc chloride supported on an active carbon carrier. A problem in this method is the difficulty in the control of the reaction temperature because the reaction is highly exothermic generating about 70 kilocalories of the heat of reaction per mole of the starting carbon tetrachloride resulting in local heating of the catalyst bed into which carbon tetrachloride and methyl alcohol are introduced jointly to disturb smooth proceeding of the reaction.

Thus, none of the above described methods is industrially quite satisfactory in one or more respects for the conversion of carbon tetrachloride into more useful and harmless chemical compounds such as methyl chloride.

SUMMARY OF THE INVENTION

The present invention accordingly has an object to provide a novel and improved method for the conversion of carbon tetrachloride into more useful and harmless compounds or, in particular, into methyl chloride by the reaction with methyl alcohol or has an object to provide an improvement in the above described fourth method by solving the problems to ensure smooth proceeding of the reaction.

Thus, the method of the present invention for the preparation of methyl chloride from carbon tetrachloride and methyl alcohol comprises the successive steps of:

(a) introducing carbon tetrachloride and water into a first reaction zone kept at an elevated temperature and filled with a solid catalyst containing, as an active catalytic ingredient, a halide or oxide of a metallic element selected from the group consisting of the elements belonging to the Group 1B, Group 2A, Group 2B, Group 4B, Group 7B and Group 8 in the Periodic Table supported on active carbon as a carrier so as to produce a gaseous reaction mixture containing carbon dioxide and hydrogen chloride by the hydrolysis of carbon tetrachloride; and (b) introducing the gaseous reaction mixture coming out of the first reaction zone and containing carbon dioxide and hydrogen chloride either as such or after condensation into a liquid form and vapor or liquid methyl alcohol into a second reaction zone kept at an elevated temperature so as to produce methyl chloride by the reaction of hydrogen chloride with methyl alcohol.

The reaction of step (b) is performed preferably in the vapor phase by introducing the gases into the second reaction zone filled with a solid catalyst which can be similar to or the same as the solid catalyst used in the reaction of step (a).

The above described inventive method comprising the steps (a) and (b) can be further improved by removing carbon dioxide from the gaseous reaction mixture coming out of the first reaction zone prior to introduction thereof into the second reaction zone. Namely, this further improved method of the invention comprises the successive steps of:

(A) introducing carbon tetrachloride and water into a first reaction zone kept at an elevated temperature and filled with a solid catalyst containing, as an active catalytic ingredient, a halide or oxide of a metallic element selected from the group consisting of the elements belonging to the Group 1B, Group 2A, Group 2B, Group 6B, Group 7B and Group 8 in the Periodic Table supported on activa carbon as a carrier so as to produce a gaseous reaction mixture containing carbon dioxide and hydrogen chloride by the hydrolysis of carbon tetrachloride;

(B) removing carbon dioxide from the gaseous reaction mixture coming out of the first reaction zone; and (C) introducing the gaseous reaction product coming out of the first reaction zone after removal of carbon dioxide either as such or after condensation into a liquid form and methyl alcohol either in the form of vapor or liquid into a second reaction zone kept at an elevated temperature so as to produce methyl chloride by the reaction of hydrogen chloride with methyl alcohol.

It is also preferable that the reaction of step (C) is conducted in the vapor phase in the second reaction zone filled with a solid catalyst which can be similar to or the same as the solid catalyst used in the reaction of step (A).

BRIEF DESCRIPTION OF THE DRAWING

The FIGURE is a block diagram of the process according to the inventive method comprising the steps of (A), (B) and (C) described above.

DETAILED DESCRIPTION OF THE PREFERRED EMBODIMENTS

As is described above, the method of the invention in the first aspect comprises two successive steps of (a) and (b), of which the step (a) conducted in the first reaction zone is a hydrolysis reaction of carbon tetrachloride with water proceeding according to the reaction equation:

$$CCl_4 + 2H_2O \rightarrow CO_2 + 4HCl.$$

This reaction, which proceeds exothermically with generation of 41 kilocalories of heat per mole of starting carbon tetrachloride, is promoted by a solid catalyst containing, as an active catalytic ingredient, a halide, e.g., chloride, or oxide of a metallic element selected from the group consisting of the Group 1B elements, e.g., copper and silver, Group 2A elements, e.g., magnesium, Group 2B elements, e.g., zinc, Group 6B elements, e.g., chromium, Group 7B elements, e.g., manganese, and Group 8 elements, e.g., iron, in the Periodic Table supported on active carbon as a carrier. Among the above named active catalytic ingredients, zinc chloride is preferred.

The reactor, usually in the form of an upright column, filled with the above described solid catalyst to form the first reaction zone is kept at an elevated temperature in the range from 150° to 250° C. or, preferably, from 200° to 220° C. and the reactants, i.e. carbon tetrachloride and water, each in the form of a vapor are introduced into the reactor, usually, at the bottom either separately or as a mixture so that carbon tetrachloride is hydrolyzed according to the above given reaction equation. When the temperature of the first reaction zone is too low, the velocity of the reaction cannot be high enough while, when the temperature is too high, the heat evolved by the reaction cannot be fully removed so that the temperature of the zone is unduly increased to cause uncontrollable running of the reaction or to cause heavy corrosion of the reactor walls. As to the mixing proportion of carbon tetrachloride and water, it is preferable that the amount of water is at least stoichiometric or, namely, at least 2 moles or, preferably, at least 2.2 moles per mole of carbon tetrachloride in order that carbon tetrachloride can be fully hydrolyzed in the first reaction zone. Although no upper limit can be defined for the amount of water relative to carbon tetrachloride, an excessively large amount of water acts as a mere diluent so that the effective capacity of the reactor would be undesirably decreased. The feed rate of the reactants into the reactor should be controlled depending on the activity of the catalyst and other factors so that the gaseous reaction mixture coming out of the first reaction zone, of which the principal ingredients are carbon dioxide and hydrogen chloride, contains an as little as possible amount of unreacted carbon tetrachloride. The pressure in this first reaction zone as well as in the second reaction zone described below is not particularly limitative but it is usually 5 kg/cm$^2$G or lower in consideration of the severe requirements for the reactor subjected to contacting with the corrosive reactant gases under such a high pressure although use of a higher pressure has an advantage that the capacity of the reactor can be increased so much.

As is described above, the reaction proceeding in the first reaction zone is a catalytic hydrolysis reaction of carbon tetrachloride. This hydrolysis reaction can proceed by using an acid-resistant zeolite as taught in U.S. Pat. No. 4,423,024. Such a zeolite catalyst, however, is less active than the solid catalyst used in the inventive method so that the reaction temperature should be as high as 220° C. or higher or, preferably, 240° C. or higher. Indeed, a reaction temperature of 240° to 332° C. is undertaken in the Examples disclosed in the above mentioned U.S. patent. When a zeolite catalyst is used in the first reaction zone according to the inventive method at a temperature of 200° C. or below, the velocity of the hydrolysis reaction is so low that a large amount of carbon tetrachloride as unreacted is discharged out of the first reaction zone. If the gaseous reaction mixture coming out of the first reaction zone and containing a large amount of unreacted carbon tetrachloride is introduced as such into the second reaction zone described below, two different reactions proceed concurrently in the second reaction zone including the hydrolysis reaction of the carbon tetrachloride and the reaction of hydrogen chloride with methyl alcohol so that an uncontrollable increase in the temperature would be resulted in the second reaction zone.

The gaseous reaction mixture coming out of the first reaction zone is then introduced into the second reaction zone kept at an elevated temperature of, for example, 150° to 250° C. together with methyl alcohol. This second reaction can be performed either in the vapor phase or in the liquid phase although the vapor-phase reaction is preferred and described below in detail. The second reaction zone is formed from a bed of a solid catalyst which can be the same one as that filling the first reaction zone although it is optional to use a catalyst of which the active catalytic ingredient is a halide or oxide of a metallic element selected from the same group as but different from that in the first reaction zone. In this second reaction zone, methyl alcohol and hydrogen chloride are reacted according to the following reaction equation:

$$CH_3OH + HCl \rightarrow CH_3Cl + H_2O,$$

to form methyl chloride and water. This reaction is also exothermic generating about 7.2 kilocalories of heat per mole of methyl alcohol or hydrogen chloride. The feeding rate of methyl alcohol should be such that the molar ratio of the hydrogen chloride introduced into the second reaction zone to the feed of methyl alcohol is in the range from 1.01 to 1.30. When this molar ratio is too small, the methyl alcohol introduced into the second reaction zone cannot be fully utilized for the reaction with hydrogen chloride and the yield of dimethyl ether as a by-product would be increased by the dehydration condensation between the molecules of methyl alcohol per se. When this molar ratio is too large, a considerable portion of the hydrogen chloride is discharged as unreacted out of the second reaction zone to cause an economical loss.

It is of course optional that the second reaction zone is formed in a second reactor separate from the first reactor for the first reaction zone. In this case, the top of the first reactor and the bottom of the second reactor are connected with a pipe line and methyl alcohol in the form of vapor are introduced into the pipe line so that the gaseous reaction mixture coming out of the first reactor is mixed with the vapor of methyl alcohol and the mixture is introduced into the bottom of the second reactor. This way with two separate reactors is advantageous in respect of the versatility in the control of the whole process because the reactions in the first and the second reaction zones can be controlled independently, for example, at different temperatures, under different pressures or by using different catalysts. When the gaseous reaction mixture coming out of the first reactor is too cold or too hot to most efficiently conduct the reaction in the second reactor, the gaseous feed into the second reactor can be pre-heated or pre-cooled to a desired temperature. Further, if necessary, the feed of methyl alcohol can be introduced partly in the form of liquid or in the form of a vapor at a relatively low temperature of, for example, 120° C. to the gaseous feed on the way through the pipe line so that the temperature of the gaseous feed to the second reactor can be greatly decreased by the latent heat of vaporization or by the sensible heat. It is further optional that hydrogen chloride obtained from other sources than the first reactor is added into the gaseous feed to the second reactor assuming a correspondingly larger capacity of the second reactor.

An alternative but more simple way to practice the inventive method is to use a single reactor in the form of a reaction column of which the lower part is utilized for the first reaction zone and the upper part is utilized for the second with or without a perforated partition wall therebetween. It is not always necessary that the upper part for the second reaction zone has a volume identical with that of the lower part for the first reaction zone. When a partition is provided between the first and the second reaction zones, an inlet port is provided on the side wall of the reactor column at a height just above the partition and methyl alcohol in the form of vapor is introduced into the reactor through this inlet port. When no partition is provided between the first and the second reaction zones, an inlet port is provided on the side wall of the reactor column at about a half height of the reactor column so that the catalyst-filled spaces below and above the inlet port serve as the first and the second, respectively, reaction zones.

The gaseous reaction product discharged out of the second reaction zone is a mixture of methyl chloride as the desired product, water vapor and unreacted hydrogen chloride, methyl alcohol and carbon tetrachloride accompanied by a minor amount of other impurity by-products. The desired methyl chloride can be separated and isolated from the mixture by any conventional method known in the art.

Although no particular difficulties in principle are encountered in this process of isolating methyl chloride from the gaseous reaction mixture, a problem is worthy to be considered in connection with removal of carbon dioxide from methyl chloride. Indeed, carbon dioxide is sometimes a by-product in various chemical processes yielding a gaseous reaction product and removed therefrom by undertaking several different methods depending on the nature of the reaction product to be purified. Typical methods for the removal of carbon dioxide from a gaseous mixture heretofore undertaken are as follows.

Firstly, the carbon dioxide-containing gaseous mixture is contacted with an alkanolamine represented by the general formula $(HOR)_nNH_{3-n}$, in which R is a divalent aliphatic hydrocarbon group and the subscript n is 1, 2 or 3, such as triethanolamine, in the presence of water at a temperature of about 50° C. under approximately atmospheric pressure so that an equilibrium is established to form an adduct of carbon dioxide to the alkanolamine according to the reaction equation:

$$2(HOR)_nNH_{3-n} + CO_2 + H_2O \rightleftharpoons [(HOR)_nNH_{4-n}]\cdot CO_2,$$

in which each symbol has the same meaning as defined above. This method, however, is not applicable to the separation of carbon dioxide from a gaseous mixture containing methyl chloride because methyl chloride also reacts with the alkanolamine to form an alkanolammonium methyl chloride expressed by the formula $$CH_3(HOR)_nNH_{3-n}Cl.$$

Secondly, the carbon dioxide-containing gaseous mixture is contacted with a hot aqueous solution of potassium carbonate at a temperature of about 120° C. under a pressure of about 20 kg/cm²G so that an equilibrium is established in the reversible reaction to form potassium hydrogen carbonate from potassium carbonate, water and carbon dioxide. This method is also not applicable to the separation of carbon dioxide from a gaseous mixture containing methyl chloride because methyl chloride also reacts with water in such a strongly alkaline medium at high temperatures to be hydrolyzed. Although the reaction can be prevented by decreasing the temperature, the velocity of carbon dioxide absorption is also greatly decreased and cannot be fully removed from the gaseous mixture unless an unpractically long absorption column is employed.

Thirdly, carbon dioxide can be removed from the gaseous mixture by the reaction with sodium hydroxide to form sodium carbonate even at such a low temperature and under such a low pressure that no reaction takes place between sodium hydroxide and methyl chloride. The reaction, however, is an irreversible reaction so that this method cannot be undertaken in a large scale unless the sodium carbonate produced in a large quantity can be advantageously and safely disposed.

In view of the above described situations in the technology for the removal of carbon dioxide from a gaseous mixture, the above proposed inventive method comprising the steps of (a) and (b) unavoidably involves a problem for the purification of methyl chloride contained in the gaseous reaction mixture coming out of the second reaction zone unless an economical method is available for the removal of carbon dioxide from the mixture. This problem, however, can be solved when the process according to the invention comprises an additional step between the steps (a) and (b) for the removal of carbon dioxide from the gaseous mixture coming out of the first reaction zone which does not contain methyl chloride.

Thus, the method of the invention can be further improved by comprising three steps of (A), (B) and (C), of which the step (A) is equivalent to step (a), step (B) is for the removal of carbon dioxide from the gaseous mixture coming out of the first reaction zone and step (C) is equivalent to step (b) except that the gaseous feed to the second reaction zone no longer contains carbon dioxide. Since the principal constituents in the gaseous output from the first reaction zone are carbon dioxide and hydrogen chloride, the carbon dioxide can be easily removed therefrom by a known method such as scrubbing of the gaseous mixture with water, condensation of the constituents other than carbon dioxide by refregeration and the like either alone or in combination.

In the following, the method of the present invention is illustrated in more detail by way of examples.

EXAMPLE 1

Two glass columns each having an inner diameter of 200 mm and a height of 500 mm as the first and the second reactors each filled with an active carbon catalyst supporting 30% by weight of zinc chloride to form a fixed catalyst bed were connected together in series with a pipe line and an inlet port for the introduction of methyl alcohol was provided on the pipe line.

While keeping the catalyst beds each at a temperature of 180° C., vapor of carbon tetrachloride heated at 150° C. and a 20% aqueous hydrochloric acid were introduced into the first reactor column at the bottom at rates of 5.87 kg (38.15 moles) per hour and 3.29 kg per hour, respectively. The feed rate of the hydrochloric acid corresponded to the rates of 858 g (23.55 moles) per hour of hydrogen chloride and 3432 g (190.75 moles) per hour of water. Vapor of methyl alcohol heated at 150° C. was introduced into the pipe line connecting the first and second reactors from the inlet port at a rate of 5.12 kg (160.14 moles) per hour and introduced into the bottom of the second reactor column together with the gaseous mixture coming out of the top of the first reactor column. The molar ratio of water to carbon tetrachloride was 5.0 and the molar ratio of chlorine contained in the carbon tetrachloride and hydrogen chloride to methyl alcohol was 1.1. The average staying times of the reactant gas on the empty column base were 10 seconds and 5.2 seconds in the first and the second reactor columns, respectively. When the reaction in the reactor columns had reached a stationary state, the temperature of the reactor columns was maintained at 200° C. in each of the first and the second reactor columns.

Table 1 below summarizes the contents of the respective constituents in the gaseous mixtures discharged out of the top of the first reactor column and out of the top of the second reactor column. The conversion of carbon tetrachloride was 98.03% at the outlet from the first reactor column and 100% at the outlet from the second reactor column and conversion of methyl alcohol was 97.53% at the outlet from the second reactor column.

COMPARATIVE EXAMPLE 1

The experiment was started in substantially the same manner as in Example 1 except that the feed of methyl alcohol was introduced into the first reactor column at the bottom thereof instead of introducing into the second reactor column through the inlet port between the first and the second reactor columns. The result was that the temperature of the first reactor column rapidly increased to exceed 300° C. without showing a sign of levelling off so that the reaction had to be discontinued.

TABLE 1

|  | 1st reactor | 2nd reactor |
|---|---|---|
| CH₃Cl | — | 7.88 kg(156.2 moles)/hr |
| CH₃OH | — | 0.13 kg(3.91 moles)/hr |
| HCl | 6.31 kg(173.1 moles)/hr | 0.73 kg(19.92 moles)/hr |
| H₂O | 2.09 kg(116.0 moles)/hr | 4.87 kg(270.7 moles)/hr |
| CCl₄ | 0.12 kg(0.75 mole)/hr | not detected |
| CO₂ | 1.64 kg(37.4 moles)/hr | 1.68 kg(38.15 moles)/hr |

COMPARATIVE EXAMPLE 2

The experimental procedure was substantially the same as in Example 1 except that the solid catalyst filling the first reactor column was replaced with an acid resistant zeolite molecular sieve (Zeolon 900-H, a product by Norton Chemical Process Products Co.). The result was that the temperature of the first reactor column could be controlled at 200° C. but the temperature of the second reactor column exceeded 200° C. finally reaching 350° C.

Table 2 below summarizes the contents of the respective constituents in the gaseous mixtures discharged out of the top of the first reactor column and out of the top of the second reactor column. The conversion of carbon tetrachloride was 44.93% at the outlet from the first reactor column and 99.83% at the outlet from the second reactor column and conversion of methyl alcohol was 97.23% at the outlet from the second reactor column.

TABLE 2

|  | 1st reactor | 2nd reactor |
|---|---|---|
| $CH_3Cl$ | — | 7.86 kg(155.8 moles)/hr |
| $CH_3OH$ | — | 0.14 kg(4.3 moles)/hr |
| HCl | 3.36 kg(93.1 moles)/hr | 0.73 kg(20.1 moles)/hr |
| $H_2O$ | 2.82 kg(156.4 moles)/hr | 4.87 kg(270.3 moles)/hr |
| $CCl_4$ | 3.23 kg(21.0 moles)/hr | 0.01 kg(0.07 mole)/hr |
| $CO_2$ | 0.75 kg(17.1 moles)/hr | 1.68 kg(38.09 moles)/hr |

EXAMPLE 2

The experiment was conducted according to the block diagram of the process illustrated in the FIGURE of the accompanying drawing.

Carbon tetrachloride was introduced into the first evaporator 1 through the inlet port 7 at a rate of 538 g/hour together with the return of diluted aqueous hydrochloric acid containing 20% by weight of hydrogen chloride from the water scrubber 4 through the pipe line 8 at a rate of 709 g/hour. These liquids were evaporated at 150° C. in the first evaporator 1. The gaseous mixture coming out of the first evaporator 1 was introduced into the bottom of the glassmade first reactor column 2 having an inner diameter of 50 mm and a height of 1000 mm with a resistance-heating wire wound therearound and filled with an active carbon catalyst supporting 30% by weight of zinc chloride. The molar ratio of water to carbon tetrachloride in the feed gas to the first reactor column 2 was 9.0 and the average staying time of the gaseous flow therethrough was 8.1 seconds on an empty column base. The temperature of the first reactor column 2 was controlled in the range from 195° to 225° C.

The gaseous reaction mixture discharged out of the first reactor column 2 at the top was introduced into the condenser 3 to effect condensation of the low boiling-point fractions. The uncondensed gaseous fraction discharged out of the condenser 3 at the top was introduced through the pipe line 9 into the water scrubber 4 under circulation of aqueous hydrochloric acid with a feed of supply water through the nozzle 11 at a rate of 1779 g/hour, from which the off-gas after absorption of the soluble matter, which contained 83.4% by weight of carbon dioxide and 16.6% by weight of water, was discharged through the vent 12 at a rate of 185 g/hour. The liquid formed by condensation in the condenser 3, which contained 33.3% by weight of hydrogen chloride and 66.7% by weight of water, was introduced through the pipe line 10 into the bottom of the second evaporator 5 at a rate of 629 g/hour. The discharge liquid from the water scrubber 4 at a rate of 2213 g/hour, which was a 20% by weight aqueous hydrochloric acid as mentioned above, was divided into two partial flows of which the first partial flow at a rate of 709 g/hour was introduced through the pipe line 8 into the first evaporator 1 as a return from the scrubber 4 while the second partial flow at a rate of 1504 g/hour was introduced through the pipe line 14 into the second evaporator 5 together with the condensate from the condenser 3.

Methyl alcohol was introduced into the second evaporator 5 through the inlet port 15 at a rate of 407 g/hour and evaporated there together with the liquid feeds from the condenser 3 and water scrubber 4. The gaseous mixture formed in the second evaporator 5 and heated at 150° C. was introduced through the pipe line 16 into the bottom of the second glass-made reactor column 6 having an inner diameter of 70 mm and a height of 1600 mm provided with an external heater coil. The second reactor column 6 was filled with the same solid catalyst as in the first reactor column 2. The molar ratio of hydrogen chloride to methyl alcohol in the feed to the second reactor column 6 was 1.1 and the average staying time of the gaseous flow therethrough was 8.5 seconds on an empty column base. The temperature of the second reactor column 6 was controlled within a range of 200° to 220° C.

The gaseous mixture discharged out of the second reactor column 6 through the outlet port 17 at a rate of 2540 g/hour contained 24.5% by weight of methyl chloride, 2.3% by weight of hydrogen chloride, 0.3% by weight of methyl alcohol, 0.08% by weight of dimethyl ether and 72.7% by weight of water. The conversion of carbon tetrachloride was already 100% in the first reactor column 2 and the conversion of methyl alcohol was 98.2% with a selectivity of 99.3% for methyl chloride.

What is claimed is:

1. A method for the preparation of methyl chloride from carbon tetrachloride and methyl alcohol which comprises the successive steps of:
   (a) introducing carbon tetrachloride and water into a first reaction zone kept at an elevated temperature and filled with a solid catalyst containing, as an active catalytic ingredient, a halide or oxide of a metallic element selected from the group consisting of the elements belonging to the Group 1B, Group 2A, Group 2B, Group 4B, Group 7B and Group 8 in the Periodic Table supported on active carbon as a carrier so as to produce a gaseous reaction mixture containing carbon dioxide and hydrogen chloride by the hydrolysis of carbon tetrachloride; and
   (b) introducing the gaseous reaction mixture coming out of the first reaction zone and containing carbon dioxide and hydrogen chloride either as such or after condensation into a liquid form and methyl alcohol into a second reaction zone kept at an elevated temperature so as to produce methyl chloride by the reaction of hydrogen chloride with methyl alcohol.

2. The method for the preparation of methyl chloride from carbon tetrachloride and methyl alcohol as claimed in claim 1 in which the reaction of step (b) is performed in the vapor phase by introducing the gaseous reaction mixture coming out of the first reaction zone and vapor of methyl alcohol into the second reaction zone filled with a solid catalyst containing, as an active catalytic ingredient, a halide or oxide of a metallic element selected from the group consisting of the elements belonging to the Group 1B, Group 2A, Group 2B, Group 6B, Group 7B and Group 8 in the Periodic Table supported on active carbon as a carrier.

3. The method for the preparation of methyl chloride from carbon tetrachloride and methyl alcohol as claimed in claim 1 in which the elevated temperature in step (a) is in the range from 150° to 250° C.

4. The method for the preparation of methyl chloride from carbon tetrachloride and methyl alcohol as claimed in claim 1 in which the active catalytic ingredient in step (a) is zinc chloride.

5. The method for the preparation of methyl chloride from carbon tetrachloride and methyl alcohol as claimed in claim 2 in which the active catalytic ingredient in step (b) is zinc chloride.

6. The method for the preparation of methyl chloride from carbon tetrachloride and methyl alcohol as claimed in claim 1 in which water and carbon tetrachloride are introduced into the first reaction zone in a molar ratio $H_2O:CCl_4$ of at least 2.2.

7. The method for the preparation of methyl chloride from carbon tetrachloride and methyl alcohol as claimed in claim 2 in which the first reaction zone and the second reaction zone are formed in a single reactor vessel.

8. A method for the preparation of methyl chloride from carbon tetrachloride and methyl alcohol which comprises the successive steps of:
  (A) introducing carbon tetrachloride and water into a first reaction zone kept at an elevated temperature and filled with a solid catalyst containing, as an active catalytic ingredient, a halide or oxide of a metallic element selected from the group consisting of the elements belonging to the Group 1B, Group 2A, Group 2B, Group 6B, Group 7B and Group 8 in the Periodic Table supported on active carbon as a carrier so as to produce a gaseous reaction mixture containing carbon dioxide and hydrogen chloride by the hydrolysis of carbon tetrachloride;
  (B) removing carbon dioxide from the gaseous reaction mixture coming out of the first reaction zone; and
  (C) introducing the gaseous reaction mixture coming out of the first reaction zone and after removal of carbon dioxide either as such or after condensation into a liquid form and methyl alcohol into a second reaction zone kept at an elevated temperature so as to produce methyl chloride by the reaction of hydrogen chloride with methyl alcohol.

9. The method for the preparation of methyl chloride from carbon tetrachloride and methyl alcohol as claimed in claim 8 in which the reaction of step (C) is performed in the vapor phase by introducing the gaseous reaction mixture coming out of the first reaction zone and freed from carbon dioxide and vapor of methyl alcohol into the second reaction zone filled with a solid catalyst containing, as an active catalytic ingredient, a halide or oxide of a metallic element selected from the group consisting of the elements belonging to the Group 1B, Group 2A, Group 2B, Group 6B, Group 7B and Group 8 in the Peri-odic Table supported on active carbon as a carrier.

10. The method for the preparation of methyl chloride from carbon tetrachloride and methyl alcohol as claimed in claim 8 in which the elevated temperature in step (A) is in the range from 150° to 250° C.

11. The method for the preparation of methyl chloride from carbon tetrachloride and methyl alcohol as claimed in claim 8 in which the active catalytic ingredient in step (A) is zinc chloride.

12. The method for the preparation of methyl chloride from carbon tetrachloride and methyl alcohol as claimed in claim 9 in which the active catalytic ingredient in step (C) is zinc chloride.

13. The method for the preparation of methyl chloride from carbon tetrachloride and methyl alcohol as claimed in claim 8 in which water and carbon tetrachloride are introduced into the first reaction zone in a molar ratio $H_2O:CCl_4$ of at least 2.2.

* * * * *